United States Patent
Geib et al.

(10) Patent No.: US 7,146,348 B2
(45) Date of Patent: Dec. 5, 2006

(54) PROBABILISTIC GOAL RECOGNITION SYSTEM AND METHOD INCORPORATING INFERRED UNOBSERVED ACTIONS

(75) Inventors: Christopher W. Geib, Minneapolis, MN (US); Robert P. Goldman, Minneapolis, MN (US)

(73) Assignee: Honeywell International Inc., Morristown, NJ (US)

( * ) Notice: Subject to any disclaimer, the term of this patent is extended or adjusted under 35 U.S.C. 154(b) by 647 days.

(21) Appl. No.: 10/286,398

(22) Filed: Nov. 1, 2002

(65) Prior Publication Data

US 2003/0139902 A1    Jul. 24, 2003

Related U.S. Application Data

(60) Provisional application No. 60/384,899, filed on May 30, 2002, provisional application No. 60/384,519, filed on May 29, 2002, provisional application No. 60/368,307, filed on Mar. 28, 2002, provisional application No. 60/351,300, filed on Jan. 22, 2002.

(51) Int. Cl.
  *G06F 17/00*   (2006.01)
  *G06N 5/02*    (2006.01)
(52) U.S. Cl. .............. 706/45; 706/46; 706/14; 706/61
(58) Field of Classification Search ........... 706/45, 706/46, 14, 61; 715/707
See application file for complete search history.

(56) References Cited

U.S. PATENT DOCUMENTS

| | | | |
|---|---|---|---|
| 4,259,548 A | 3/1981 | Fahey et al. | |
| 4,418,269 A | 11/1983 | Eaton-Williams | |
| 4,803,625 A | 2/1989 | Fu et al. | |
| 4,952,928 A | 8/1990 | Carroll et al. | |
| 5,086,385 A | 2/1992 | Launey et al. | |
| 5,128,035 A | 7/1992 | Clack et al. | |
| 5,228,449 A | 7/1993 | Christ et al. | |
| 5,400,246 A | 3/1995 | Wilson et al. | |
| 5,410,471 A | 4/1995 | Alyfuku et al. | |
| 6,021,403 A * | 2/2000 | Horvitz et al. | 706/45 |
| 6,233,570 B1 * | 5/2001 | Horvitz et al. | 706/11 |
| 6,260,035 B1 * | 7/2001 | Horvitz et al. | 706/60 |
| 6,262,730 B1 * | 7/2001 | Horvitz et al. | 715/707 |
| 6,421,655 B1 * | 7/2002 | Horvitz et al. | 706/61 |
| 2004/0070091 A1 | 4/2004 | Rotering et al. | |

FOREIGN PATENT DOCUMENTS

EP    0 558 975 A1    2/1993
WO    WO 01/075653 A3    10/2001

OTHER PUBLICATIONS

A copy of PCT International Search Report mailed Sep. 9, 2004 (6 pgs).

* cited by examiner

*Primary Examiner*—Joseph P. Hirl
(74) *Attorney, Agent, or Firm*—Kris T. Fredrick

(57) ABSTRACT

A system and method for recognizing a goal of an actor in an environment by considering hypothesized unobserved actions. The method includes providing a plan library that includes a list of possible goals and corresponding plans. Actions of the actor are observed, and the occurrence of hypothesized unobserved actions are considered. Finally, one or more plans consistent with the observed actions and the consideration of hypothesized unobserved actions are identified.

27 Claims, 8 Drawing Sheets

PROBABILISTIC GOAL RECOGNITION SYSTEM AND METHOD INCORPORATING INFERRED UNOBSERVED ACTIONS

CROSS-REFERENCE TO RELATED APPLICATIONS

This application is related to, and is entitled to the benefit of, and U.S. Provisional Patent Application Ser. No. 60/351,300, filed Jan. 22, 2002; U.S. Provisional Patent Application Ser. No. 60/368,307, filed Mar. 28, 2002; U.S. Provisional Patent Application Ser. No. 60/384,899, filed May 30, 2002; and U.S. Provisional Patent Application Ser. No. 60/384,519, filed May 29, 2002; the teachings of all of which are incorporated herein by reference.

BACKGROUND OF THE INVENTION

The present invention relates to a probabilistic, abductive system and method for recognizing goals or plans of an actor or agent. More particularly, it relates to a system and method that utilizes observed activities in conjunction with hypothesized unobserved activities to probabilistically recognize a goal/plan of an actor or agent. Application domains include automated monitoring and response systems for daily living environments, computer network security, and competitive analysis, to name but a few.

The concept of automatically recognizing or predicting a goal or intent of an actor or agent based upon tracked events has been the subject of intensive research efforts. Countless domain applications could benefit from such a system or model. Unfortunately, the complexities of these domains have heretofore prevented formulation of a truly useful intent recognition system or model. As a point of reference, the terms "actor" and "agent" are used interchangeably throughout this specification, and relate to human and non-human subjects.

One potential application for an intent recognition device relates to a human actor monitoring and support system. In this regard, the evolution of technology has given rise to numerous, discrete devices adapted to make daily, in-home living more convenient. For example, companies are selling microwaves that connect to the internet, and refrigerators with computer displays, to name but a few. These and other advancements have prompted research into the feasibility of a universal home control system that not only automates operation of various devices or appliances within the home, but also monitors activities of an actor in the home. Such a system could further perform device control based upon the actor's activities and/or events in the living space.

In general terms, such an automated human actor monitoring and response system will consist of a suite of sensors in the living space to detect actor actions and environment states, a set of actuators that control devices in the environment as well as facilitate communication with the actor (and others), and a computer system (local or remote) capable of making decisions to assist the actor. With respect to this "assistance" feature, a necessary attribute resides in not only understanding what actions or plans the actor has already completed, but also inferring goals of the actor, or more simply, "what is the actor trying to do". By knowing the actor's intended goals or plans, the system would be able to "pre-emptively" respond. For example, with intent or goal inference capabilities, the monitoring and response system could lock a door before a demented actor attempted to leave his/her home, provide next step-type suggestions to an actor experiencing difficulties with a particular activity or task, suppress certain warning alarms in response to a minor kitchen fire upon recognizing that the actor is quickly moving toward the kitchen, etc.

Artificial intelligence research has produced preliminary models for achieving plan recognition of an actor or agent that could be potentially applied to one or more domains of interest. For example, Kautz, H. and Allen, J. F., "Generalized Plan Recognition," *Proceedings of the Fifth National Conference on Artificial Intelligence*, pp. 32–38 (1986) defined the problem of plan recognition as the problem of identifying a minimal set of top-level actions sufficient to explain the set of observed actions. To a first approximation, in their formulation the problem of plan or intent recognition is viewed as a problem of graph covering.

Others, such as Charniak, E. and Goldman, R. P., "A Bayesian Model of Plan Recognition," *Artificial Intelligence*, 64 (1); 53–79 (1993), have recognized that since plan recognition involves abduction, it could best be done as a Bayesian inference. Bayesian inference supports the preference for minimal explanations, in the case of hypothesis that are equally likely, but also correctly handles explanations of the same complexity but different likelihoods.

Further probabilistic-based efforts have addressed the problems of influences from the state of the world and evidence from failure to observe. For example, Goldman, R. P., Geib, C., and Miller, C., "A New Model of Plan Recognition," *Proceedings of the 1999 Conference on Uncertainty in Artificial Intelligence*, Stockholm, (July 1999), advance an abductive, probabilistic theory of plan recognition that accounts for the accumulative effect of a sequence of observations of partially-ordered, interleaved plans and the effect of context on plan adoption.

While probabilistic plan recognition is a preferred method for inferring the goals of an agent, as it results in a measure of the likelihood for each hypothesized plan, the previously-advanced techniques fail to account for unobserved actions. That is to say, existing work on plan recognition has assumed complete observability of the agent's actions. However, implementation of a probabilistic plan recognition system into actual working environments, such as part of an in-home monitoring and response system, must account for the fact that complete observability of all actions is virtually impossible to achieve.

For example, relative to the exemplary in-home monitoring and support domain, sensors will inevitably fail to detect an action or event (e.g., due to sensor malfunction). Requiring that this "missed" action or event occur (or be "sensed") before the model "recognizes" a particular goal will overly limit the overall usefulness of the system. Unfortunately, the ability to consider that unobserved actions have occurred, as part of an overall probabilistic evaluation is inherently problematic, as consideration of potentially unobserved actions results in a significant expansion of the problem's search space.

In addition to an in-home actor monitoring and support system, a number of other domains would clearly benefit from an efficacious intent recognition system or model. For example, a computer network security system capable of recognizing the intended goals of a hacker, and then taking necessary steps to stop the hacker's efforts would be highly advantageous. In most, if not all, of these potential domains, truly effective intent recognition requires that unobserved actions be accounted for. Unfortunately, this feature has not been fully perfected with current methodologies. Therefore, a need exists for a system and method of probabilistically recognizing a goal of an actor or agent based upon the inferred presence of unobserved actions, with the system and method being applicable in various domains such as in conjunction with an in-home monitoring and response system.

SUMMARY OF THE INVENTION

A system and method for recognizing a goal of an actor in an environment by considering hypothesized unobserved actions. The method includes providing a plan library that includes a list of possible goals and corresponding plans. Actions of the actor are observed, and the occurrence of hypothesized unobserved actions are considered. Finally, one or more plans consistent with the observed actions and the consideration of hypothesized unobserved actions are identified.

DESCRIPTION OF THE PREFERRED EMBODIMENTS

A. Context of Probabilistic Intent Recognition Applications

Figure 1:
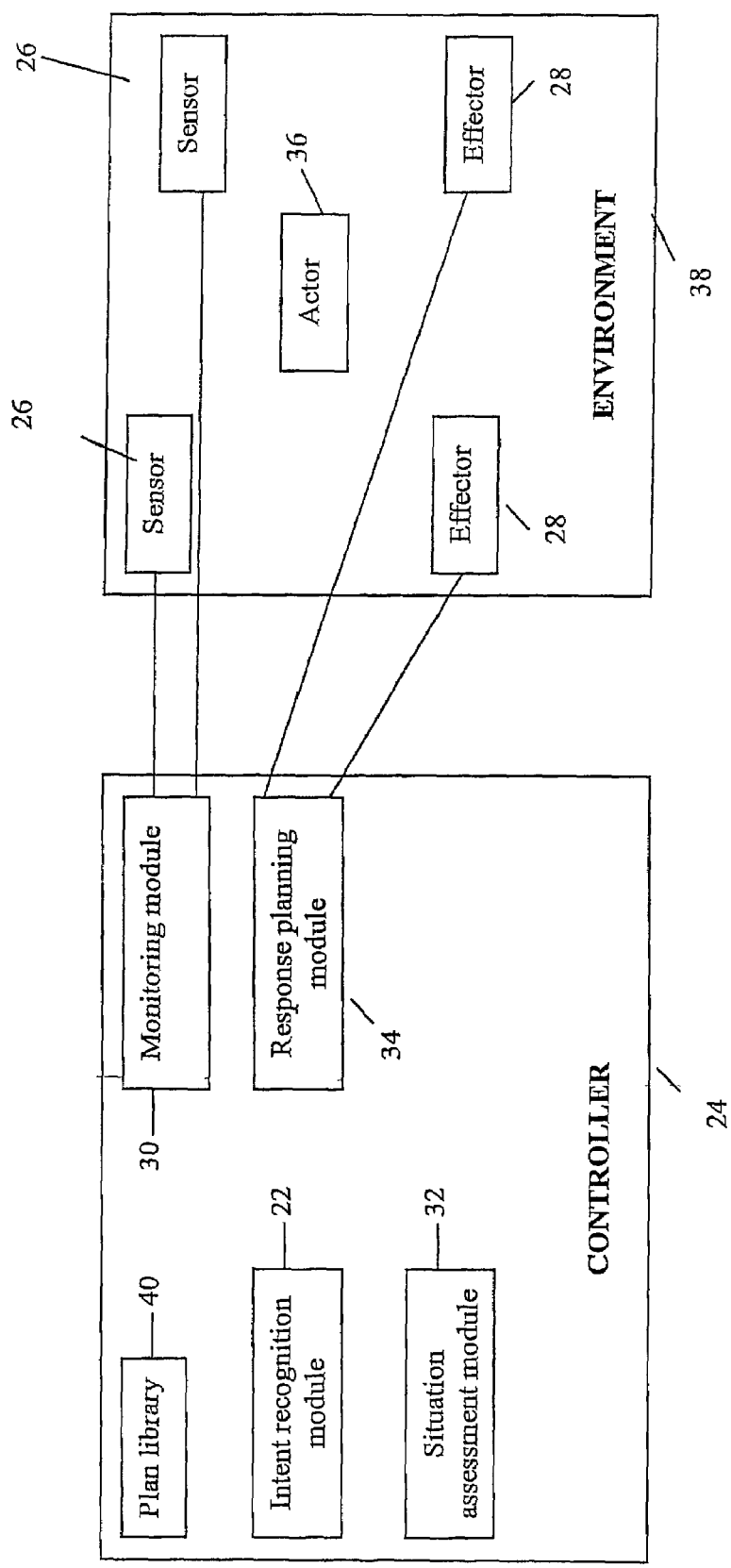
FIG. 1 is a block diagram of an embodiment of the probabilistic plan recognition system of the present invention applied in an in-home actor monitoring and response system environment.

The present invention relates to a system and method of probabilistically recognizing a goal of an actor or agent that accounts for the possible occurrence or execution of unobserved actions, preferably as part of the operation of an automated monitoring and response system for an actor in a daily living environment. Alternatively, the system and method of the present invention are applicable to other domains (e.g., computer security, industrial control environments, etc.). Relative to but one preferred application, FIG. 1 provides an exemplary illustration, in block form, of an intent recognition module 22 in accordance with the present invention as part of a monitoring and response system 20. The system 20 can assume a variety of forms, but preferably includes a controller 24, a plurality of sensors 26, and one or more actuators or effectors 28. As described in greater detail below, the intent recognition module 22 is preferably provided as part of the controller 24 that further includes other components such as a monitoring module 30, a situation assessment module 32, and a response planning module 34. Of course, depending upon the particular domain application of the intent recognition module 22, one or more of the sensors 26, effectors 28 and/or modules 30–34 can be modified or eliminated.

With respect to the actor monitoring and response system 20 application, and in general terms, the sensors 26 actively, passively, or interactively monitor activities of an actor or user 36, as well as segments of the actor's environment 38. Information or data from the sensors 26 is signaled to the controller 24 for interpretation by the monitoring module 30. The situation assessment module 32 processes information from the monitoring module 30 to determine what the actor 36 is doing and what is happening in the actor's environment 38. The intent recognition module 22 operates in conjunction with (or as part of) the situation assessment module 32 and determines what the actor 36 is intending to do. The response planning module 34, in turn, generates appropriate responses based upon information from the situation assessment module 32 and the intent recognition module 22, and generates appropriate responses that are carried out via the actuators 28.

The key component associated with the exemplary system 20 resides in the intent recognition module 22 and an ability of the module 22 to account for unobserved actions, as described below. As such, the sensors 26, the actuators 28, as well as other modules or portions thereof (e.g., the monitoring module 30, the situation assessment module 32 and/or the response planning module 34) can assume a wide variety of forms. Preferably, the sensors 26 are networked by the controller 24. The sensors 26 can be non-intrusive or intrusive, active or passive, wired or wireless, physiological or physical. In short, the sensors 26 can include any type of sensor that provides information relating to the activities of the actor 36 or other information relating to the actor's environment 38. For example, in the home monitoring domain, the sensors 26 can include motion detectors, pressure pads, door latch sensors, panic buttons, toilet-flush sensors, microphones, cameras, fall-sensors, door sensors, heart rate monitor sensors, blood pressure monitor sensors, glucose monitor sensors, moisture sensors, etc. In addition, one or more of the sensors 26 can be a sensor or actuator associated with a device or appliance used by the actor 36, such as stove, oven, telephone, television, security pad, medication dispenser, thermostat, etc., with the sensor or actuator 26 providing data indicating that the device or appliance is being operated by the actor 36 (or someone else).

Similarly, the actuators or effectors 28 can also assume a wide variety of forms. In general terms, the actuators or effectors 28 are configured to control operation of a device in the actor's environment 38 and/or to interact with the actor 36. Examples of applicable actuators or effectors 28 include computers, displays, telephones, pagers, speaker systems, lighting systems, fire sprinklers, door lock devices, pan-tilt-zoom controls on a camera, etc.

The controller 24 is preferably a microprocessor-based device capable of storing and operating the various modules illustrated in FIG. 1, including the intent recognition module 22. With respect to the modules 22, 30–34, each can be provided as individual agents or software modules designed around fulfilling the designated function. Alternatively, one or more of the modules 22, 30–34 can instead be a grouping or inter-working of several modules or components that, when operated by the controller 24, serve to accomplish the designated function. Even further, separate modules can be provided for individual subject matters that internally include the ability to perform one or more of the desired functions. Details on preferred implementation techniques, as well as other preferred modules useful with the system 20, are provided, for example, in U.S. Provisional Application Ser. No. 60/368,307, filed Mar.28, 2002 and entitled "System and Method for Automated Monitoring, Recognizing, Supporting, and Responding to the Behavior of an Actor", the teachings of which are incorporated herein by reference.

B. Plan Library 40

With the above in mind, in one preferred embodiment the intent recognition module 22 preferably provides a means for probabilistically recognizing an intended goal or plan of the actor 36. In this regard, the intent recognition module 22 interacts with a plan library or database 40. In general terms, the intent recognition module 22 incorporates simple hierarchical (task decomposition) plans, and references information in the plan library 40, observed actions and hypothesized unobserved actions to recognize or evaluate the likelihood that the actor 28 is engaged in a particular plan otherwise described in the plan library 40.

The plan library 40 stores a listing of possible goals of the actor 28, along with "recipes" for achieving each of those goals. In particular, a sub-listing of at least one plan is provided for each goal. Within each plan, an activity plan graph is provided that consists of required primitive actions for completing the corresponding plan. In a preferred embodiment, entries in the plan library 40 may be viewed as an "and/or tree". An example hierarchical plan library for an in-home actor monitoring and support domain is provided in diagrammatical form in FIG. 2. The plan library lists three possible root goals (referenced in FIG. 2 as "G") of "Feed-dog," "Eat," and "Answer-phone".

Figure 2:
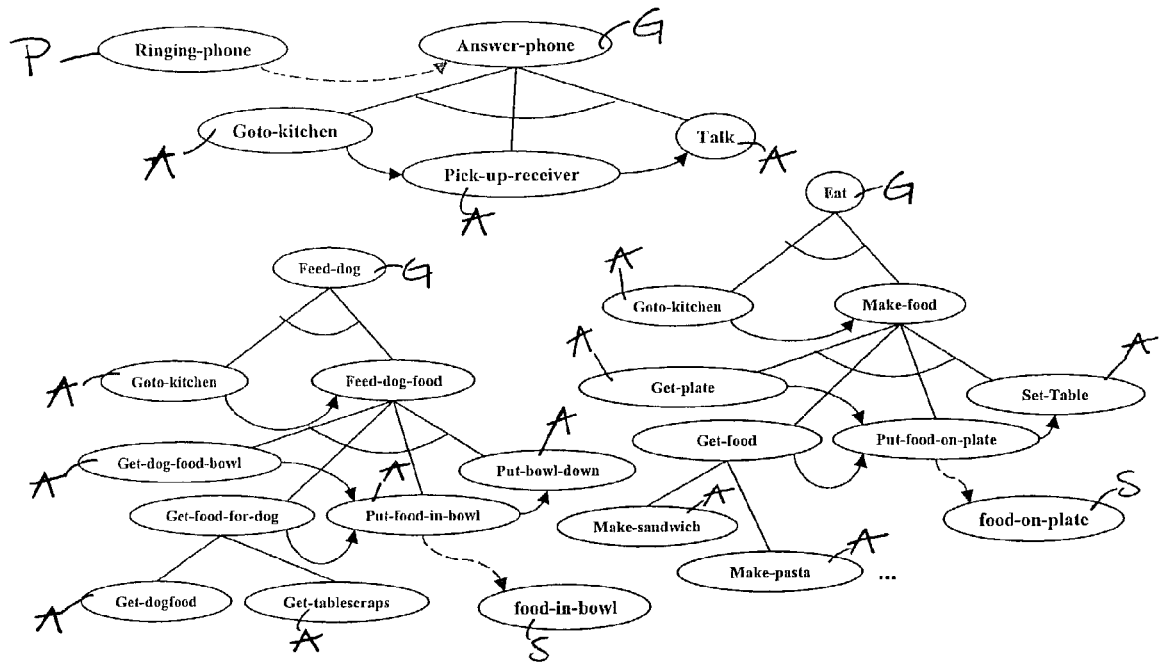
FIG. 2 is a diagrammatical illustration of an exemplary plan library useful in an in-home actor monitoring and response system environment.

Each and/or tree defines a decomposition of the root goal into sequences of sub-actions that will achieve the root goal. With respect to the one example plan library 40 of FIG. 2, such a decomposition is indicated by a straight solid line from the parent node to each of the children. If all of the sub-actions must be done to achieve the parent goal, the parent goal is represented as an "and node" in the tree, and is illustrated in FIG. 2 by an arc crossing all of the links from the parent to the children. For example, the "Feed-dog-food" sub-goal requires that each of "Get-dog-food-bowl," "Get-food-for-dog," "Put-food-in-bowl" and "Put-bowl-down" occur for the action to be successful.

In many cases, the sub-steps of an "and node" must be done in a particular order. Ordering constraints between the actions are represented by directed arcs in the plan graph of FIG. 2. For example, in the "Answer-phone" plan definition, ordering constraints require that "Goto-kitchen" occur before "Pick-up-receiver", and that "Pick-up-receiver" occur before "Talk". Conversely, certain actions of a particular plan graph may not be ordered with respect to each other. For example, relative to the "Feed-dog" root goal, "Get-dog-food-bowl" or "Get-food-for-dog" can occur in any order, but both must occur before "Put-food-in-bowl".

A goal or sub-goal can also be defined by a set of possible expansions, such that any single expansion can be executed to achieve the goal. In this case, the actor/agent executing the plan would naturally or purposefully "choose" exactly one of the expansions. Such choice points in the plan definitions are indicated by "or nodes". With respect to the sample plan library 40 of FIG. 2, this is illustrated by the absence of an "and arc" crossing the children's links to their parent node. For example, to achieve "Get-food-for-dog," the agent/actor need (or must) only execute one of "Get-dog food" or "get-tablescraps".

The definitions of plans are terminated in leaf nodes that represent "primitive actions" that are candidates for being observed in the domain (referenced in FIG. 2 as "A").

Where applicable, a particular plan tree may further include a state precondition ("P" in FIG. 2; e.g., "Ringing-phone" is a state precondition for "Answer-phone" root goal) and/or a state change or an effect of actions ("S" in FIG. 2; e.g., "Food-in-bowl" is a state change for the "Feed-dog" root goal, and "Food-on-plate" is a state change for the "Eat" root goal). Connection between a state precondition or state change and the corresponding plan graph is represented by a broken line in FIG. 2.

Figure 3:
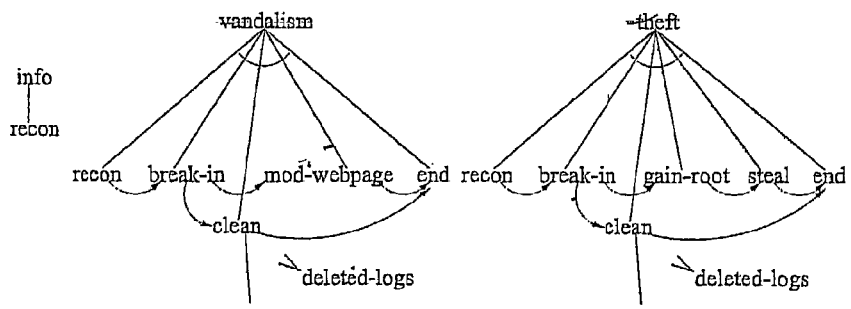
FIG. 3 is a diagrammatical illustration of an exemplary plan library useful in a computer network security system environment.

It will be recognized that the plan library 40 provided in FIG. 2 is but one example of limitless goals, plans, and plan graphs. Depending upon the complexity of the system 20 installation, the plan library 40 can provide for countless possible goals each having multiple plans and extensive plan graphs. Contents of the plan library 40 are domain-specific, and the present invention is not limited to a daily living environment monitoring domain. For example, the intent recognition module 22 can be used in a computer security system domain and include information relating to goals such as stealing information from a computer or vandalizing web pages. An exemplary hierarchical plan library in diagrammatical form for a computer network security domain is provided in FIG. 3. Alternatively, the intent recognition module 22 can be used in industrial control applications such as oil refineries, with the related plan library 40 including goal/plan graph information specific to the industrial installation.

Information in the plan library 40 is preferably entered by the actor 36 and/or others familiar with the expected constraints of the particular installation, expected activities, expected actor intents/goals, etc. Additionally or alternatively, the system 20 can include a machine learning module (not shown) that, either alone in combination with other modules, generates and/or revises information stored in the plan library 40.

C. Example of A Specific Probabilistic Intent Recognition Framework

Regardless of the exact contents of the plan library 40, the intent recognition module 22 is adapted to utilize goal/plan information from the plan library 40 in conjunction with observed actions of the actor 36 and/or within the actor's environment 38 (via the monitoring module 30) to generate a set of execution traces that provide a basis for probalistically indicating the most likely goal of the actor 36. One preferred probabilistic-based technique for performing this analysis is provided below.

In general terms, the intent recognition module 22 generates and records an observed action stream based upon the observed actions of the actor and/or the actor's environment 38. The observed action stream provides a sequential listing of observed actions. The observed action stream is then compared against the plan library 40, and potentially corresponding plan graphs (and thus corresponding goals) are selected. The selected plan graphs are then used as the basis for generating a set of explanations that each include the observed action stream and at least a portion of the selected activity plan graph.

Figure 4:
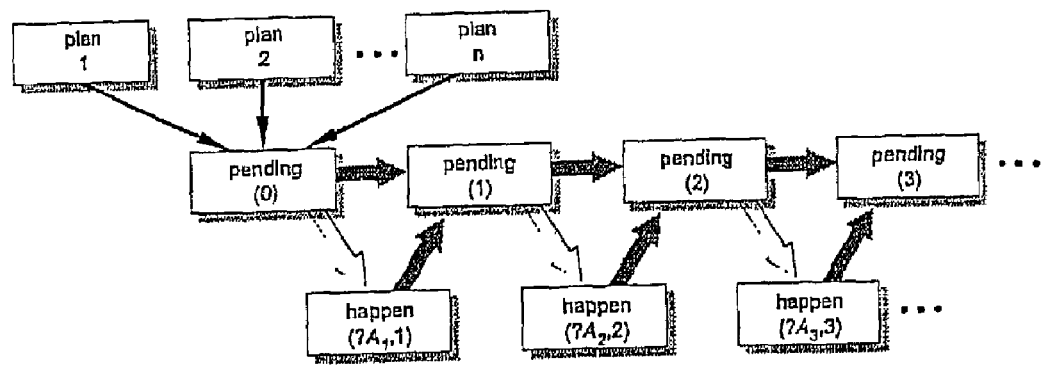
FIG. 4 is a block diagram representation of a pending set generation model.

One preferred model of plan recognition is described in Goldman, R. P., Geib, C., and Miller, C., "A New Model of Plan Recognition," *Conference on Uncertainty in Artificial Intelligence,* Stockhölm (July 1999), the teachings of which are incorporated herein by reference. In general terms, the preferred plan recognition model is based on the realization that plans are executed dynamically and that at any given moment, the actor or agent is able to choose to execute any of the actions that have been enabled by the actor's or agent's previous actions. To formalize this slightly, initially the actor or agent has a set of goals and chooses a set of plans to execute to achieve these goals. The set of plans chosen determines the set of pending primitive actions. As the actor or agent continues engaging in a particular activity, the actor or agent will select and execute one of the pending actions, thereby generating a new set of pending actions from which further actions will be chosen. The new pending set is generated from the previous set by removing the action just executed and adding newly enabled actions. Actions become enabled when their required predecessors are completed. This process is illustrated in FIG. 4. To provide some intuition for the probabilistically-inclined, the sequence of pending sets can be seen as a Markov chain.

The above view of plan execution provides a simple conceptual model for the generation of execution traces. To use this model to perform probabilistic plan recognition, the preferred methodology hypothesizes a set of goals for the actor and utilizes the plan library 40 (FIG. 1) to engage in forward simulation of the actor's hypothesized goals. This process only considers simulations that are consistent with the observed actions in the order in which they are observed. As part of the simulation, the actor's pending sets are generated to determine if one or more of the goals in the plan library 40 are consistent with actual observations of actions of the actor and/or the actor's environment. The resulting combination of an execution trace, with consistent pending set(s) and hypothesized goal(s), is referred to as an "explanation" of what the actor may be doing/intending to do.

The above process is repeated, varying the hypothesized goals and how the observed actions contribute to those goals to generate the complete and encompassing set of all possible explanations for the observed actions. Since this set of explanations for the observations is generated to be exclusive and exhaustive, a probability distribution can be established over the set. Based upon this probability distribution, an evaluation can be performed to determine which of the hypothesized possible goals the actor 36 is most likely pursuing.

In accordance with one preferred model embodiment, computing the probability of a given root goal is a two-step process. First, the conditional probability of each explanation is established. Second, this conditional probability is used to compute the conditional probability of each of the root goals. In one preferred implementation, the conditional probability of a specific explanation of a given set is determined by:

$$P(\exp_1 \mid obs) = \prod_{i=1}^{I} P(root_i) \cdot \prod_{j=1}^{J} \left( \frac{1}{|method_j|} \right) \cdot \prod_{k=1}^{K} (1/|\text{Pendion } Set_k|) \quad \text{Equation 1}$$

where:
$\exp_1$=the specific explanation or execution trace;
obs=observed activity stream;
I=total number of goals/root intentions in $\exp_1$;
$root_i$=ith root goal/intent in $\exp_1$;
$P(root_i)$=prior probability of $root_i$;
J=number of choices of "or nodes" in $\exp_1$;
$method_j$=jth choice/"or node" in $\exp_1$;

$|method_j|$=number of alternative possible expansions for $method_j$;
K=|obs|;
Pending $Set_k$=pending set at time k; and
|Pending $Set_k$|=size of the pending set at time k.

The conditional probability for each root goal is generated by dividing the sum of the conditional probabilities of all the explanations that have the root goal by the sum of all the explanations of the observations.

The above model is but one technique for probabilistically recognizing a plan or intent, and is in no way limiting to the present invention. Importantly, however, the one exemplary model, like all other available models, does not address the issue of unobserved actions. As described below, the system and method of the present invention extends the probabilistic model, whatever its form, to account for unobserved actions.

D. Extending the Probabilistic Intent Recognition Model to Consider Unobserved Actions Returning to FIG. 1, regardless of the exact technique by which the execution traces are generated, analyzed or otherwise utilized for generating further information from which a probabilistic evaluation can be performed, the system and method of the present invention provides the intent recognition module 22 with an ability to consider not only directly observed actions of the actor 36 and/or events in the environment 38, but also potentially unobserved actions or events as part of the execution trace generating process. In particular, the intent recognition module 22 is adapted to introduce and reason about unobserved actions within a probabilistic framework. This consideration, previously unaddressed in the realm of probabilistic intent recognition, is highly important for successful implementation of the intent recognition module 22. For example, relative to the in-home monitoring and response system 20 domain, instances of a particular sensor 26 malfunctioning or otherwise failing to detect a particular activity will undoubtedly occur from time-to-time. Were the execution traces limited to activity plan graphs (and thus related goals) that only exactly matched (in terms of required primitive actions) the observed action stream, a sensor malfunction may result in the intent recognition module 22 failing to consider the correct plan (and thus related goal) the actor 36 was engaged in. Simply stated, it is not sufficient to simply assume that the observed action stream is complete. The system and method of the present invention overcomes this deficiency by constructing a set of possible execution traces, inserting hypothesized unobserved actions to complete them.

One preferred implementation of this process is to again use the plan library 40 to engage in forward simulation of the observation stream. However, rather than using the observation stream as the sole determiner of which actions are executed next, a choice point is added. Instead of only considering explanations that account for the next action in the observed stream, the preferred method of the present invention considers explanations in which any listed action in the associated pending set is hypothesized as possibly having been done but not observed. The preferred methodology still requires that all actions in the observation stream eventually become part of the explanation being considered. However, hypothesized, unobserved actions that are consistent with the pending set can be "inserted" into the explanation being considered. It is recognized that in theory, unbounded insertion of hypothesized unobserved actions will result in a significant expansion of the space of possible or considered explanations. The preferred system and method of the present invention addresses this potential issue as described below.

With respect to the one preferred probabilistic intent recognition model described above, the generation of explanations that include unobserved actions entails determining the conditional probability of the explanations. As such, an additional term is added to the previous equation as follows:

$$P(exp_1 \mid obs) = \prod_{i=1}^{I} P(root_i) \cdot \prod_{j=1}^{J} \left( \frac{1}{|method_j|} \right) \cdot$$

$$\prod_{k=1}^{K} (1/|\text{Pending } Set_k|) \cdot \prod_{l=1}^{L} P(unob_l)$$

Equation 2 where:
exp$_1$=the specific explanation or execution trace;
obs=observed activity stream;
I=total number of goals/root intentions in exp$_1$;
root$_i$=ith root goal/intent in exp$_1$;
P(root$_i$)=prior probability of root$_i$;
J=number of choices of "or nodes" in exp$_1$;
method$_j$=jth choice/"or node" in exp$_1$;
|method$_j$|=number of alternative possible expansions for methods$_j$;
K=|number of actions (observed and unobserved) in the explanation|;
|Pending Set$_k$|=size of the pending set at time k;
L=number unobserved primitive actions in exp$_1$;
unob$_l$=lth unobserved leaf node or primitive action; and
P(unob$_l$)=prior probability that unob$_l$ is executed and is not observed.

The system and method of the present invention is preferably further adapted to include guidelines for terminating the consideration process. As a point of reference, other probabilistic intent recognition algorithms or models (that do not otherwise account for unobserved actions) are "terminated" when the complete set of observations are explained. Since the system and method of the present invention adds unobserved actions, this termination criterion is no longer sufficient. Instead, the system and method determines the likelihood that various actions have been executed and were not observed to evaluate when to stop adding hypothesized unobserved actions to a proposed execution trace. In this regard, not all actions are equally likely to be executed without detection. Some actions are harder to hide than others. For example, the probability that a person could make a small change in the amount of air entering into their home undetected is much higher than the probability that they could successfully turn off the entire HVAC system of the home unnoticed. By capturing the probability that an action can be executed without observation, it is possible for the system and method of the present invention to generate the probability of a sequence of actions being executed unobserved. In addition, the system and method bounds the probability of the unobserved actions with an explanation that the actor or user (or others associated with installation and operation of the intent recognition module 22) are willing to accept.

If no threshold were placed on the likelihood of unobserved actions, the process of inferring actions would proceed to successively more and more unlikely explanations by adding more and more unobserved actions. To prevent the generation of this infinite sequence of ever less likely explanations of the actor's intent/goal (via resultant execution traces), the system and method of the present invention preferably requires a threshold probability value for the unobserved actions be provided. The execution traces are then constructed as previously described. For any execution trace including at least one hypothesized unobserved action, the likelihood of that unobserved action(s) being executed unnoticed is determined. If this determined likelihood is less than the pre-determined threshold value, the execution trace is eliminated from further consideration. In effect, the system and method of the present invention allows the user (or others) to specify how unlikely an explanation they are willing to accept, and then use this bound to limit the unobserved actions that are added to the execution trace. Alternatively, a more straightforward fixed or known upper bound on the number of unobserved actions that can be inserted into any particular execution trace can be provided.

In order to bound the unobserved actions, the last term of Equation 2 above is critical, and a running total is maintained for this term. Given the probability threshold value (T) (selected and entered by the user) and an acceptable execution trace, the hypothesized execution trace must satisfy the following equation:

$$T \le \prod_{l=1}^{L} P(unob_l) \text{ if } L > 0$$

Equation 3

Figure 5:
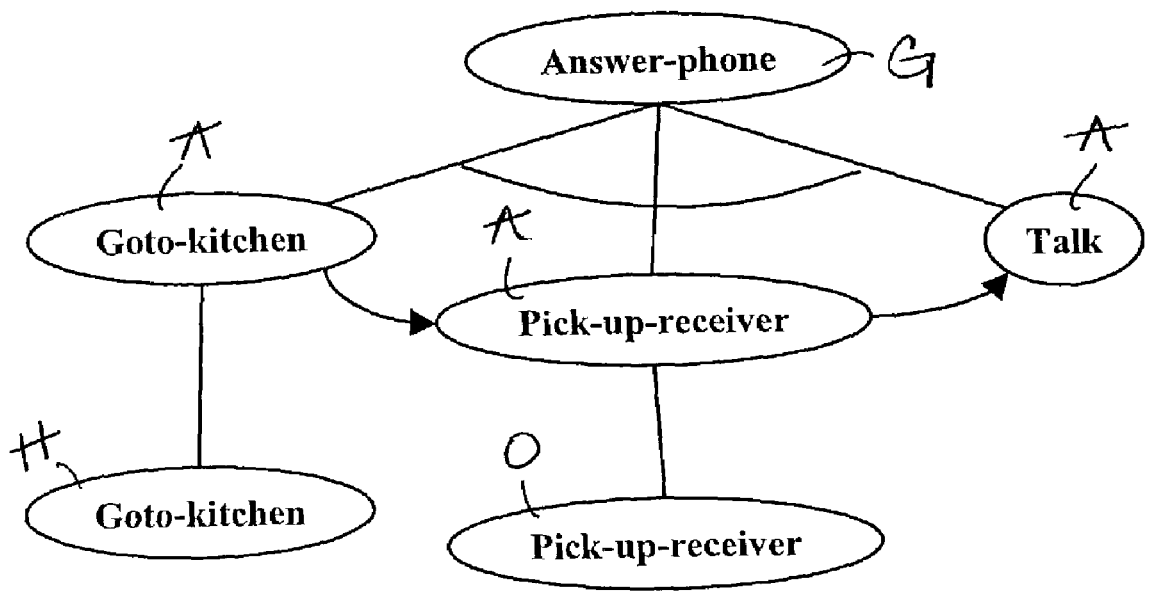
FIG. 5 is a diagrammatical illustration of an exemplary execution trace generated by the system and method of the present invention based upon the plan library of FIG. 2.

To better illustrate the effect of considering unobserveds, reference is made to the plan library of FIG. 2. Relative to this plan library, assuming an observed action stream of ["Pick-up-receiver"], if unobserved actions were not accounted for, the "Answer-phone goal" would not be considered (nor would the "Feed-dog" or the "Eat" goals) since observed action stream does not include "Goto-kitchen". However, by hypothesizing that "Goto-kitchen" was unobserved and inserting it into the corresponding execution trace (e.g., ["Goto-kitchen", "Pick-up-receiver"]), the "Answer-phone" goal would be considered as part of the probabilistic plan evaluation. This relationship is shown diagrammatically in FIG. 5, with the observed event of "Pick-up-receiver" designated by "O" and the hypothesized, unobserved event of "Goto-kitchen" denoted as "H".

Although the above example is highly simplistic, it is recognized that simply assuming that every possible action was unobserved will significantly expand the search space. The system and method of the present invention prunes this space through ordering constraints provided by the observations. In particular, if a plan graph (possibly containing more than a single root goal and associated plans) does not contain all of the observed actions of the observed action stream, or if the observed action stream does not obey the ordering constraints imposed by the plan graph, that particular plan graph can be filtered from consideration and not be used as a basis for an execution trace.

Figure 6:
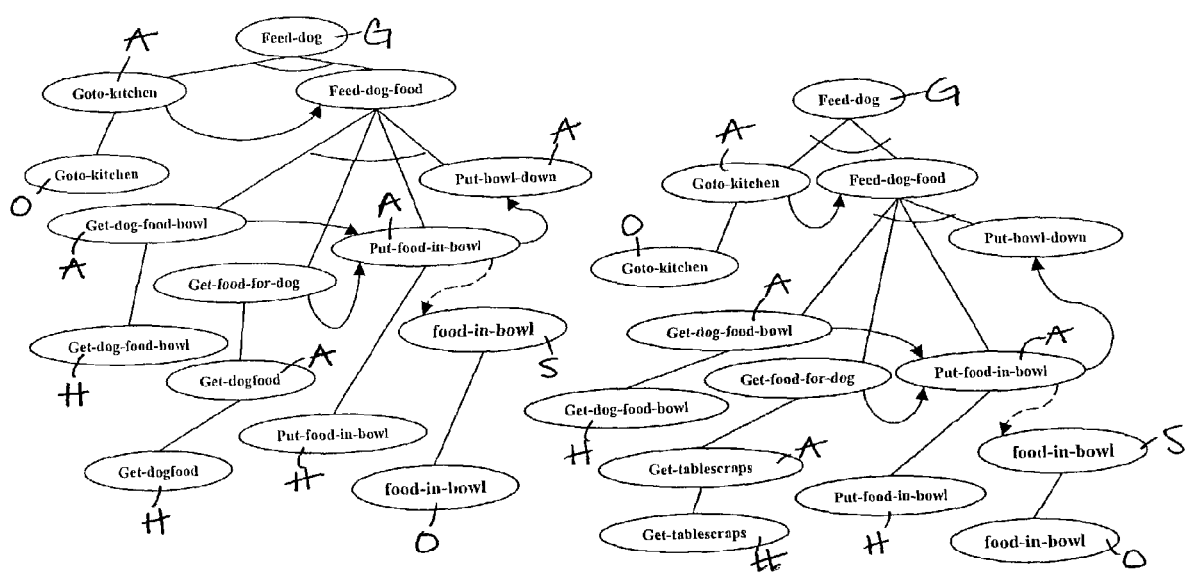
FIG. 6 is a diagrammatical illustration of exemplary execution traces generated by the system and method of the present invention based on the plan library of FIG. 2.

Additionally, unobserved actions can be inferred from state changes. In particular, while a particular sensor may fail to detect performance of an action, the resulting effects of that action can still be "observed" by other sensors. Thus, a reported state change can provide evidence or otherwise indicate occurrence of unobserved action(s) that would give rise to the reported desired effect. From them, it can be inferred that the action must have occurred before the report of the state change. Reports of state change can also simply provide confirming information about a previously observed action. For example, and referring to the plan library of FIG. 2, consider an observed action stream of ["Goto-kitchen", "Food-in-bowl"]. A report of "Food-in-bowl" (or state change) implies that "Put-food-in-bowl", "Get-dog-food-bowl", and one of "Get-dog-food" or "Get-tablescraps" have occurred unobserved. Further, the ordering constraints in the plan library imply that they must fall between execution of "Goto-kitchen" and "Food-in-bowl". Thus, state change reports give more information about the execution traces that are consistent with the observation. As a point of further explanation, FIG. 6 illustrates in diagrammatical form the possible execution traces resulting from the above example, with observed actions being denoted as "O" and inserted, hypothesized unobserved actions identified as "H".

In a preferred embodiment, the intent recognition module 22 (FIG. 1) is adapted to perform the state change processing based upon an assumption that there is only a single report for a given state change. This preferred feature obviates potential processing complications whereby multiple sensors each reporting the same state change will not cause the intent recognition module 22 to believe that the given proposition has changed state more than once. Essentially, "chattering" sensors that would otherwise produce multiple reports of the same state change are filtered.

In addition, the possible execution traces that otherwise include at least one hypothesized unobserved action are also filtered to be consistent with the unobserved actions that are implied by unenabled actions. In this regard, an "unenabled action" is one that is observed without having first observed the actions the plan library specifies must come before it. For example, considering again the plan library provided in FIG. 2, and in particular the "Feed-dog" and "Eat" root goals, where an observed action stream of ["Get-dog food", "Make-sandwich"] is observed, it can be concluded that these actions are members of disjoint plans; that is, no single root goal will explain both of these actions. However, these actions are even more informative since they are both unenabled by the observed actions. With respect to this hypothetical observed action stream, the plan library of FIG. 2 specifies that "Goto-kitchen" must occur before "Get-dog-food" and "Make-sandwich". Therefore, in order to explain these two observations, it can be hypothesized that "Goto-kitchen" has been executed unobserved. Thus, these two actions provide evidence of two distinct plans: ["Goto-kitchen", "Get-dog-food"] and ["Goto-kitchen", "Make-sandwich"]. Unenabled actions provide more information for use in reconstructing the actor's actual actions than other observations. They require that the action itself be in the sequence, but they also provide evidence of unobserved actions. Relative to the generation of execution traces based upon the above example, the set of observations can allow pruning of any execution sequence or trace that does not contain "Get-dog-food", followed sometime later by a "Make-sandwich", but it also dictates that any execution trace that does not have "Goto-kitchen" preceding "Get-dog-food" should be ignored. These unenabled actions are very important pieces of information when attempting to infer the plans of the actor.

The above described system and method for probabilistically accounting for unobserved actions in the context of automated intent or goal recognition overcomes problems identified with previous intent recognition methodologies. The execution traces generated by the system and method of the present invention can be analyzed in a number of different manners (one specific example of which is provided below). However, considering hypothesized unobserved actions as a part of the execution trace generation process, and preferably in conjunction with the threshold bound, will allow the system to handle domains that are otherwise too complex for existing methodologies.

E. Example of Unobserved Actions Within Specific Probabilistic Intent Recognition Framework As previously described, the set of execution traces generated by the above algorithm (that otherwise were probabilistically deemed acceptable), includes one or more hypothesized unobserved actions, and are utilized by the intent recognition module 22 (FIG. 1) to probabilistically recognize or estimate an intention or goal of the actor or agent depending upon the particular domain application.

Figure 7A:
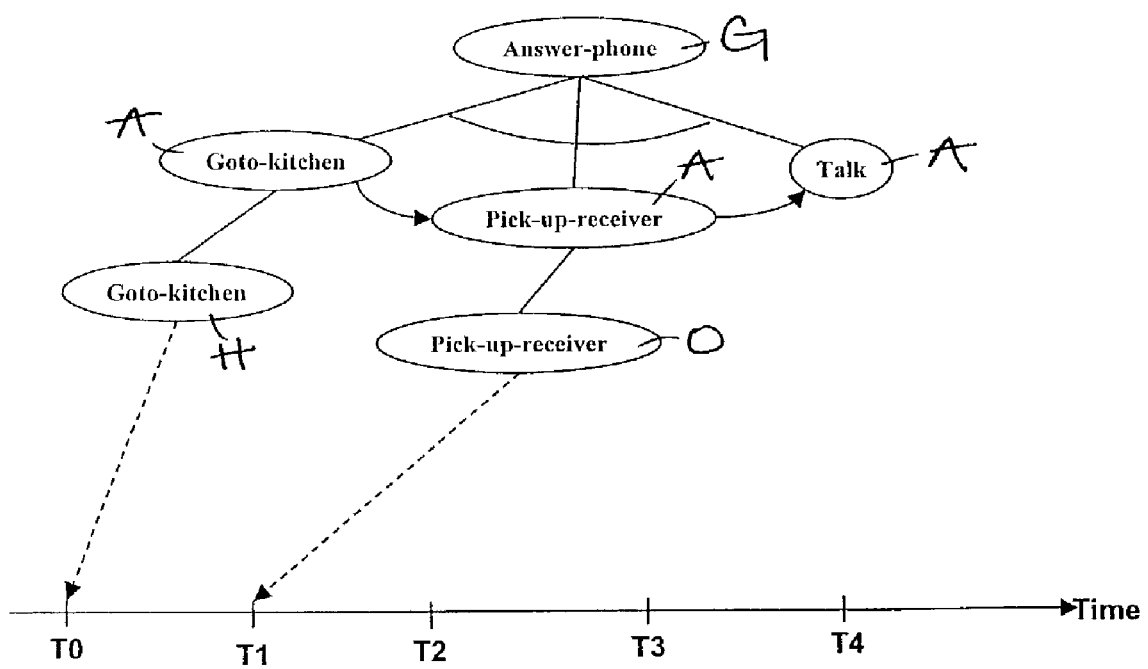
FIGS. 7A–7G are diagrammatical illustrations of possible goal explanations generated by the system and method of the present invention in accordance with a hypothetical observed event.
Figure 7B:
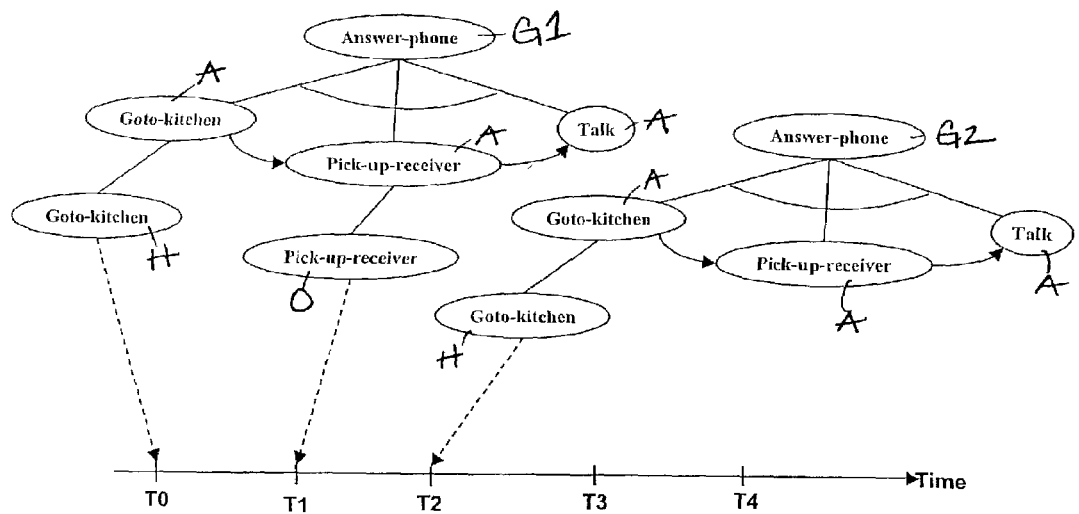
Figure 7C:
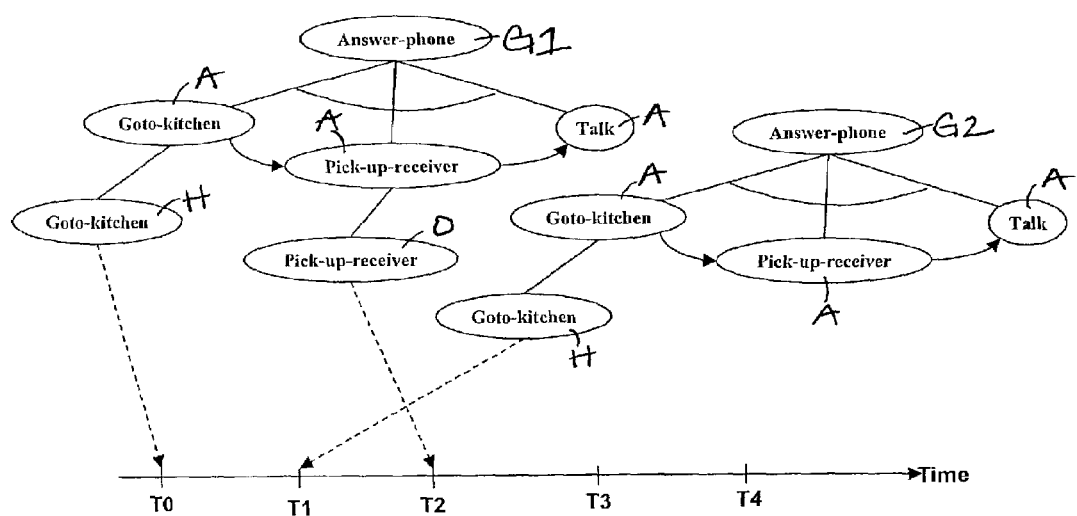

With continued reference to the plan library of FIG. 2, a hypothetical observation stream consists of a single ["Pick-up-receiver"] event. Assuming a set threshold limit sufficient to allow two unobserved "Goto-kitchen" events but no others, the single "Pick-up-receiver" observation would result in seven possible explanations or execution traces, shown diagrammatically in FIGS. 7A–7G. FIG. 7A illustrates a first possible explanation of a single "Answer-phone" goal dictated by "Goto-kitchen" being unobserved at time T0 followed by the observed "Pick-up-receiver" at time T1. FIG. 7B illustrates a second possible explanation characterized by two "Answer-phone" goals, one ("G1") dictated by "Goto-kitchen" unobserved at time T0 followed by the observed "Pick-up-receiver" at time T1; the other "Answer-phone" goal ("G2") dictated by a hypothesized, unobserved "Goto-kitchen" at time T2. FIG. 7C illustrates a third possible explanation again characterized by two "Answer-phone" goals. However, unlike the second possible explanation, the first goal ("G1") of the third possible explanation are supported by "Goto-kitchen" being unobserved at time T0 and the observed "Pick-up-receiver" at time T2; the other "Answer-phone" goal ("G2") is supported by "Goto-kitchen" observed at time T1.

Figure 7D:
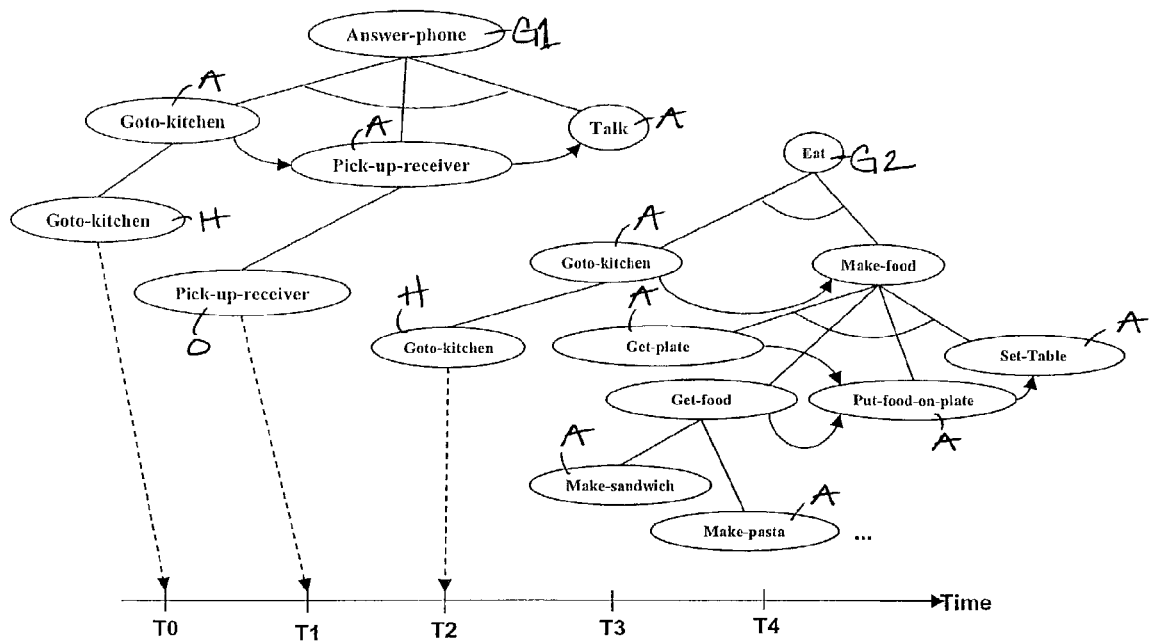
Figure 7E:
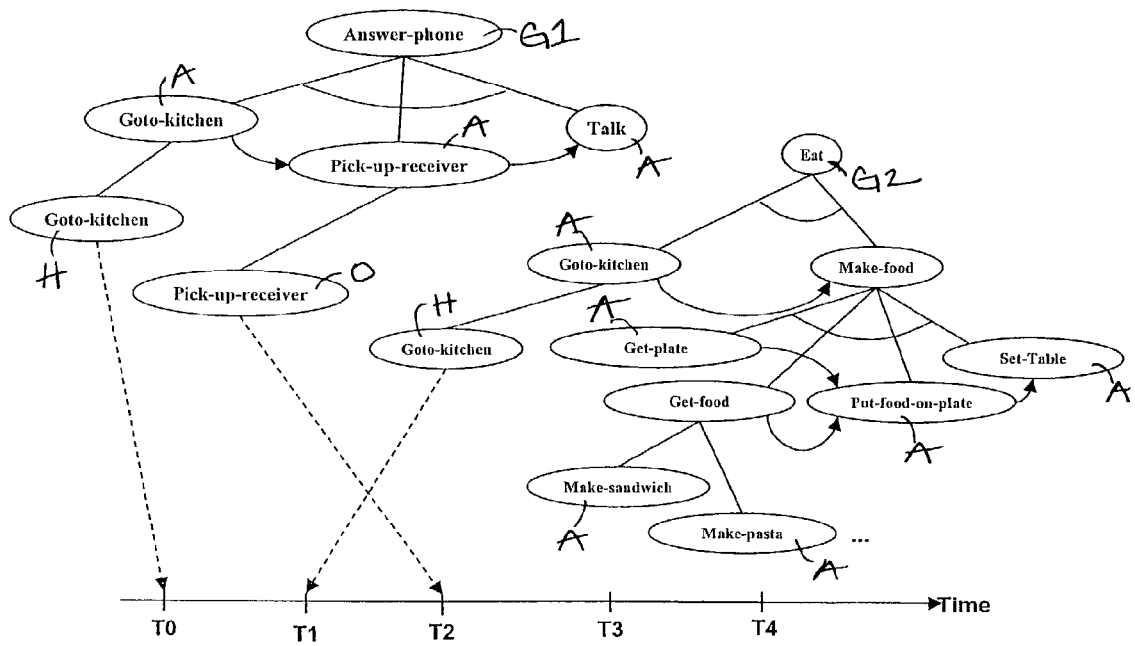

A fourth possible explanation, characterized by one "Answer-phone" goal ("G1") and one "Eat" goal ("G2"), is shown in FIG. 7D. The "Answer-phone" goal is supported by the unobserved "Goto-kitchen" at time T0 followed by the observed "Pick-up-receiver" at time T1; the "Eat" goal is dictated by hypothesizing that "Goto-kitchen" was unobserved at time T2. A fifth explanation, illustrated in FIG. 7E, is similar to the explanation of FIG. 7D in that it includes an "Answer-phone" goal ("G1") and an "Eat" goal ("G2"). However, the ordering of unobserveds varies (accounting for the possibility that the actor may decide to eat before answering the phone). In particular, the "Answer-phone" goal of FIG. 7E is supported by "Goto-kitchen" unobserved at time T0 and the observed "Pick-up-receiver" at time T2; the "Eat" goal is supported by hypothesizing that "Goto-kitchen" occurred unobserved at time T1.

Figure 7F:
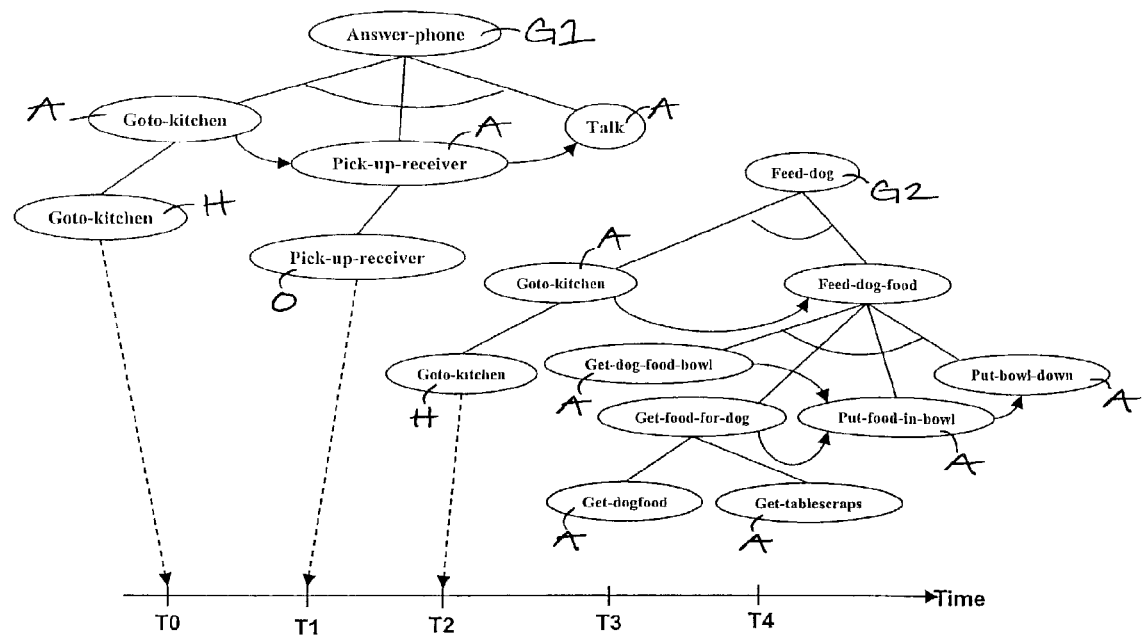
Figure 7G:
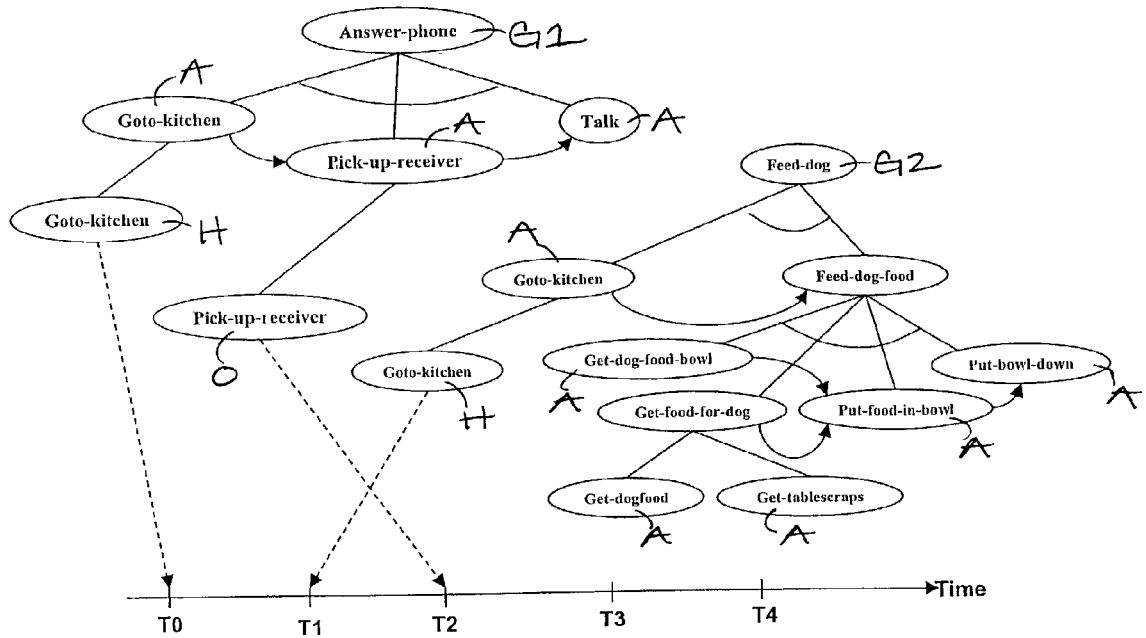

FIG. 7F illustrates a sixth possible explanation that includes the goals of "Answer-phone" ("G1") and "Feed-dog" ("G2"). The "Answer-phone" goal is explained by hypothesizing that "Goto-kitchen" was observed at time T0 followed by the observed "Pick-up-receiver" at time T1; the "Feed-dog" goal is supported by hypothesizing that "Goto-kitchen" was unobserved at time T2. Conversely, the ordering of the "Answer-phone" and "Feed-dog" goals can be reversed, as reflected in the seventh possible explanation of FIG. 7G. In particular, the "Answer-phone" goal ("G1") is supported by hypothesizing an unobserved occurrence of "Goto-kitchen" at time T0 followed by the observed "Pick-up-receiver" event at time T2; the "Feed-dog" goal ("G2")

of the seventh explanation is supported by hypothesizing an unobserved "Goto-kitchen" event at time T1.

It will be recognized that the above-described probabilistic methodology for recognizing a goal of an actor is but one available technique. Other probabilistic-based frameworks can also be applied. Regardless of the exact approach, however, the intent recognition module 22 (FIG. 1) of the present invention incorporates the ability to extend the observed sequence of actions with hypothesized unobserved actions consistent with the observed actions, observed state changes, and the plan graphs to create a set of possible execution traces. The resulting execution traces are then used as the basis for the probabilistic evaluation, such as that described above (e.g., the set of execution traces are used to construct pending sets and then the probability distribution over the sets of hypotheses of goals and plans implicated by each of the traces and pending sets). The resulting information generated by the intent recognition module 22 can then be used by or with the situation assessment module 32 (FIG. 1) in evaluating the actor's 36 (FIG. 1) current situation and needs, as well as to formulate appropriate responses (in conjunction with the response planning module 34 (FIG. 1)). As such, the system and method of the present invention provides a marked improvement over previous designs.

Although the present invention has been described with respect to preferred embodiments, workers skilled in the art will recognize that changes can be made in form and detail without departing from the spirit and scope of the present invention. For example, the probabilistic goal recognition with hypothesized unobserved actions system and method of the present invention have been preferably described with respect to the domain of an in-home actor monitoring and response system. Alternatively, a number of other domains are equally applicable such as network computer security, competitive analysis, detecting terrorists, assistant systems for pilots, etc.

What is claimed is:

1. An automated method of recognizing a goal of an actor in an environment, the method comprising:
   providing a plan library including a listing of possible goals and plans to accomplish each of the possible goals, each of the plans comprising a plurality of actions for completing the plan;
   observing actions relative to the actor;
   considering whether hypothesized unobserved actions have occurred; and
   identifying one or more plans consistent with the observed actions and the considered occurrence of hypothesized unobserved actions.

2. The method of claim 1, further comprising:
   probabilistically evaluating the identified plans to designate a most likely goal of the actor.

3. The method of claim 2, wherein the step of probabilistically evaluating includes determining a probability distribution over the set of consistent plans.

4. The method of claim 1, wherein considering whether hypothesized unobserved actions have occurred includes:
   identifying at least one primitive action in one of the plans that is not otherwise one of the observed actions;
   designating the at least one primitive action as a potential hypothesized unobserved action; and
   evaluating whether the potential hypothesized unobserved action is likely to have occurred.

5. The method of claim 4, wherein evaluating the potential hypothesized unobserved action includes:
   probabilistically determining whether the potential hypothesized unobserved action is enabled by one or more of the observed actions.

6. The method of claim 4, wherein evaluating the potential at least one hypothesized unobserved action includes:
   probabilistically determining whether the potential hypothesized unobserved action is consistent with an observed state change.

7. The method of claim 4, wherein evaluating the potential hypothesized unobserved action includes:
   establishing a probabilistic threshold value for unobserved actions;
   probabilistically determining a likelihood of the potential hypothesized unobserved action having occurred relative to the observed actions; and
   determining whether the determined likelihood is less than the probabilistic threshold value.

8. The method of claim 4, wherein a plurality of hypothesized unobserved actions are considered.

9. The method of claim 1, wherein the plans in the plan library are modeled as partially ordered plan graphs.

10. The method of claim 1, wherein the actor is a human actor operating in a daily living environment.

11. The method of claim 10, wherein observing actions includes:
    providing a plurality of sensors in the daily living environment, each adapted to provide information indicative of at least one of an action of the actor and an event in the environment; and
    reviewing information from the plurality of sensors.

12. The method of claim 11, wherein the plurality of sensors includes at least one sensor selected from the group consisting of a motion detector, pressure pad, door latch sensor, panic button, toilet-flush sensor, microphone, camera, fall sensor, heart rate sensor, blood pressure monitor sensor, glucose monitor sensor, moisture sensor, and appliance actuator sensor.

13. The method of claim 1, wherein the actor is an unauthorized user operating in a computer network environment.

14. The method of claim 13, wherein observing actions includes:
    monitoring usage of the computer network.

15. A computer assisted system for recognizing a goal of an actor in an environment, the system comprising:
    an information input device for generating information indicative of actions of the actor;
    a plan library including a listing of possible goals, wherein each goal includes a sub-listing of at least one plan for accomplishing the corresponding goal upon completing the corresponding plan, each plan including a sub-listing of primitive actions for performing that plan; and
    a controller adapted to:
      receive information from the information input device,
      record observed actions,
      consider whether hypothesized unobserved actions have occurred,
      identify one or more plans consistent with the observed actions and the considered occurrence of hypothesized unobserved actions.

16. The system of claim 15, wherein the controller is further adapted to probabilistically evaluate the identified plans for designating a most likely goal of the actor.

17. The system of claim 16, wherein the controller is further adapted to determine a probabilistic distribution over the set of consistent plans.

18. The system of claim 15, wherein the controller is further adapted to:
identify at least one primitive action in one of the plans that is not otherwise one of the recorded observed actions;
designate the at least one primitive action as a potential hypothesized unobserved action; and
evaluate whether the potential hypothesized unobserved action is likely to have occurred.

19. The system of claim 18, wherein the controller is further adapted to:
probabilistically determine whether the potential hypothesized unobserved action is enabled by one or more of the observed actions.

20. The system of claim 18, wherein the controller is further adapted to:
probabilistically determine whether the potential hypothesized unobserved action is consistent with an observed state change.

21. The system of claim 18, wherein the controller is further adapted to:
store a probabilistic threshold value for unobserved actions;
probabilistically determine a likelihood of the potential hypothesized unobserved action having occurred relative to the observed actions; and
determine whether the determined likelihood is less than the probabilistic threshold value.

22. The system of claim 15, wherein the plans in the plan library are modeled as partially ordered plan graphs.

23. The system of claim 15, wherein the controller is further adapted to perform monitoring functions relating to a human actor operating in a living space environment.

24. The system of claim 23, wherein the information input device includes a plurality of sensors adapted to sense activities of the human actor in the living space.

25. The system of claim 24, further comprising:
an effector linked to the controller and adapted to control operation of a device in the living space.

26. The system of claim 15, wherein the controller is further adapted to perform a response planning function based upon a determined goal of the actor.

27. The system of claim 15, wherein controller is further adapted to perform monitoring functions of an unauthorized user operating in a computer network environment.

* * * * *